United States Patent [19]

Sasajima et al.

[11] 4,065,565
[45] Dec. 27, 1977

[54] ACYLHYDRAZONES AND ANTI-PSYCHOTIC COMPOSITIONS THEREOF

[75] Inventors: Kikuo Sasajima, Toyonaka; Keiichi Ono, Nishinomiya; Masaru Nakao, Toyonaka; Isamu Maruyama, Minoo; Shigenari Katayama; Shigeho Inaba, both of Takarazuka; Hisao Yamamoto, Kobe, all of Japan

[73] Assignee: Sumitomo Chemical Company, Limited, Osaka, Japan

[21] Appl. No.: 603,813

[22] Filed: Aug. 12, 1975

[30] Foreign Application Priority Data

Aug. 13, 1974 Japan .................................. 49-92985

[51] Int. Cl.² .......................................... C07D 241/04
[52] U.S. Cl. ................... 424/250; 260/268 R; 260/268 PH; 260/293.6; 260/293.66; 260/293.78; 260/295 K; 260/558 H; 260/562 H; 424/263; 424/267
[58] Field of Search ......... 260/268 R, 268 PH, 293.6, 260/293.66, 293.78, 293.58, 295 K; 424/250, 267

[56] References Cited
U.S. PATENT DOCUMENTS 3,890,323  6/1975  Yamamoto et al. ............. 260/268 R
3,925,387  12/1975  Maruyama et al. ........... 260/268 PH Primary Examiner—Henry R. Jiles
Assistant Examiner—Richard A. Schwartz
Attorney, Agent, or Firm—Birch, Stewart, Kolasch and Birch

[57] ABSTRACT

Acylhydrazone compounds having excellent pyschotropic activity which are represented by the formula:

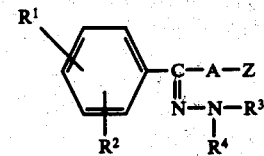

wherein Z is selected from the groups having the formulas:

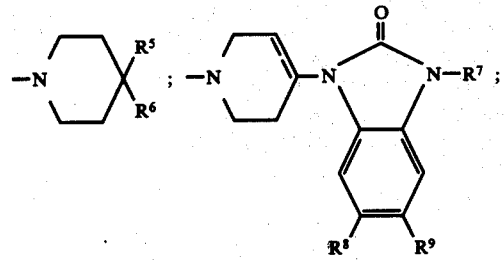

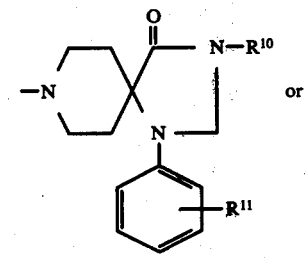

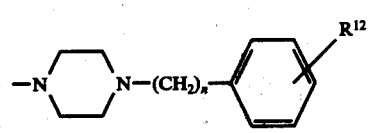

wherein $n$ is an integer of from 0 to 2 and $R^1$–$R^{12}$ are as defined hereinbelow.

9 Claims, No Drawings

ACYLHYDRAZONES AND ANTI-PSYCHOTIC COMPOSITIONS THEREOF

The present invention relates to novel acylhydrazone compounds and their production. More particularly, it relates to pharmacologically active acylhydrazone compounds having the following general formula (I) and their non-toxic pharmaceutically acceptable salts, and their production and use:

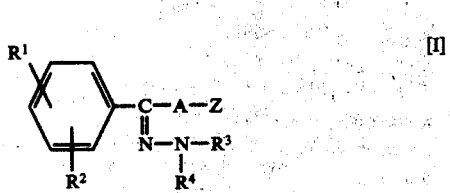

wherein $R^1$ and $R^2$ are each a hydrogen atom, a halogen atom, a lower alkyl group, a lower alkoxy group, an acylamino group, an N-lower alkylacylamino group, an N-ar(lower)-alkylacylamino group, an N,N-di(lower)alkylamino group, a nitro group or a trifluoromethyl group, $R^3$ is a hydrogen atom or a lower alkyl group, $R^4$ is an acyl group, A is a lower alkylene group and Z is a group of either one of the formulas:

(wherein $R^5$ is a hydrogen atom, an acyloxy group or a hydroxyl group and $R^6$ is a hydrogen atom or a phenyl or benzyl group optionally substituted with one or two substituents selected from the group consisting of halogen, lower alkyl, lower alkoxy and trifluoromethyl on the benzene ring);

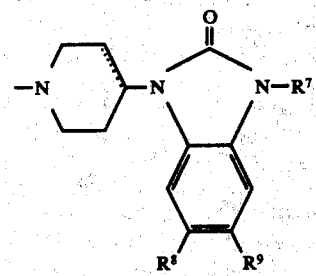

(wherein the dotted line indicates the optional presence of an additional single bond linkage, $R^7$ is a hydrogen atom or a lower alkyl group and $R^8$ and $R^9$ are each a hydrogen atom, a halogen atom or a lower alkyl group);

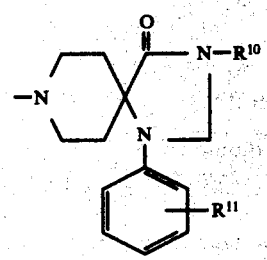

(wherein $R^{10}$ is a hydrogen atom or a lower alkyl group and $R^{11}$ is a hydrogen atom, a halogen atom, a lower alkyl group or a lower alkoxy group); and

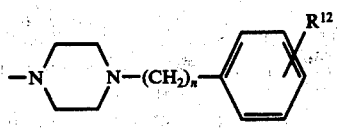

(wherein $R^{12}$ is a hydrogen atom, a halogen atom, a lower alkyl group, a lower alkoxy group or a trifluoromethyl group and n is an integer of from 0 to 2).

In the definitions as used herein, the term "lower alkyl" is intended to mean alkyl groups having from one to about four carbon atoms such as methyl, ethyl, n-propyl, isopropyl, n-butyl, sec.-butyl and t-butyl. The term "lower alkoxy" means alkoxy groups having from one to about four carbon atoms such as methoxy, ethoxy, n-propoxy, isopropoxy, n-butoxy, sec.-butoxy and t-butoxy. The term "halogen" may include fluorine, chlorine, bromine and iodine. By the term "acyl" in acylamino, lower alkylacylamino, ar(lower)alkylacylamino, acyloxy and acyl, the following groups are meant: benzoyl optionally substituted with one or two substituents selected from the group consisting of halogen, lower alkyl and lower alkoxy, lower alkanoyl (e.g. acetyl, n-propionyl, isobutyryl, n-butyryl), cycloalkylcarbonyl (e.g. cyclopropylcarbonyl, cyclohexylcarbonyl), lower alkenoyl (e.g. propenoyl, butenoyl), phenyl(lower)alkanoyl, halo(lower)alkanoyl, amino(lower)alkanoyl, phenoxy(lower)alkanoyl, lower alkylamino(lower)alkanoyl, lower alkoxy(lower)alkanoyl, phenyl(lower)alkenoyl (e.g. cinnamoyl), etc. The term "lower alkylene" may have 1 to about four carbon atoms and represent methylene, ethylene, trimethylene, tetramethylene, etc.

As the result of an extensive study on acylhydrazone derivatives, it has been found that the acylhydrazone compounds [I] have excellent pharmacological properties as anti-psychotic agents without causing any appreciable side effect.

Among the acylhydrazone compounds [I], those wherein A is trimethylene display particularly excellent anti-psychotic properties when evaluated by central anti-catacholaminergic and cholinergic activity tests in animals. They, for instance, show higher anti-apomorphine activity with much weaker or no catalepsy in rats than chlorpromazine. (Catalepsy is regarded as the measure of the extrapyramidal side effect common to conventional anti-psychotic agents).

The acylhydrazone compounds [I] wherein A is methylene, ethylene or tetramethylene show therapeutically desirable central anti-cholinergic properties when evaluated by the anti-tremorine test in animals.

The acylhydrazone compounds [I] generally have a variety of useful pharmacological properties such as activity on the central and autonomic nervous system, anti-adrenergic, and analgesic activities. From this point of view, preferred are those in which A is trimethylene, $R^1$ is halogen at the p-position and $R^2$ is halogen, hydrogen or acylamino. More preferred are those in which A is trimethylene, $R^1$ is fluorine at the p-position, $R^2$ is hydrogen or halogen, $R^3$ is hydrogen, and $R^4$ is benzoyl, lower alkanoyl, phenyl(lower)alkanoyl, cycloalkylcarbonyl or phenoxy(lower)alkanoyl.

Accordingly, a basic object of the present invention is to provide the acylhydrazone compounds [I]. Another object of this invention is to provide a process for producing the acylhydrazone compounds [I]. A further object of the invention is to provide a pharmaceutical composition comprising at least one of the acylhydrazone compounds [I] as an active ingredient. These and other objects will be apparent to those skilled in the art to which the present invention pertains from the foregoing and subsequent descriptions.

According to the present invention, the acylhydrazone compound [I] can be prepared by (A) reacting a hydrazone compound of the formula:

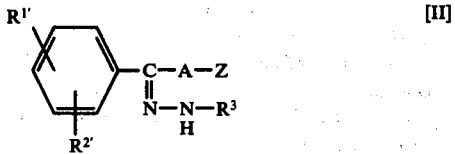

wherein $R^{1'}$ and $R^{2'}$ are each a hydrogen atom, a halogen atom, a lower alkyl group, a lower alkoxy group, an amino group, an N,N-di(lower)alkylamino group, an N-lower alkylamino group, an N-ar(lower)alkylamino group, an acylamino group, an N-lower alkylacylamino group, a nitro group or a trifluoromethyl group and $R^3$, A and Z are each as defined above with an acylating agent or (B) reacting a ketone compound of the formula:

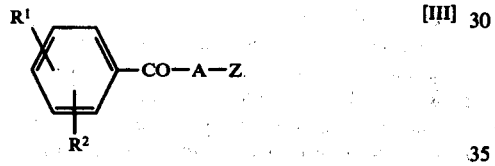

wherein $R^1$, $R^2$, A and Z are each as defined above with an acylhydrazine compound of the formula:

wherein $R^3$ and $R^4$ are each as defined above.

The hydrazone compound [II] can be prepared by reacting the ketone compound [III] with a hydrazine compound of the formula: $NH_2NHR^3$ wherein $R^3$ is as defined above.

The reaction of the hydrazone compound [II] with the acylating agent is usually carried out in an inert solvent such as an aromatic hydrocarbon (e.g. benzene, toluene, xylene), an amide (e.g. dimethylformamide, dimethylacetamide) or an ether (e.g. dioxane, diethylether, tetrahydrofuran) at a temperature within a range of −50° C to the boiling point of the solvent. Further, it is possible to use a basic substance such as an alkali carbonate (e.g. sodium carbonate, potassium carbonate), an alkali hydrogen carbonate (e.g. sodium hydrogen carbonate, potassium hydrogen carbonate), an alkali hydroxide, (e.g. sodium hydroxide, potassium hydroxide) or an organic amine (e.g. pyridine, triethylamine) as an acid binding agent. Even if such basic substance is not used, the reaction may favorably proceed.

The acylating agent may be the corresponding acid halide or acid anhydride: for example, lower alkanoyl halide (e.g. acetyl chloride, acetyl bromide, propionyl chloride), benzoyl halide, substituted benzoyl halide, lower alkenoyl halide (e.g. propenyl chloride), phenyl(lower)alkanoyl halide (e.g. phenylacetyl chloride) phenoxy(lower)alkanoyl halide (e.g. phenoxyacetyl chloride), phenyl(lower)alkenoyl halide (e.g. cinnamoyl chloride), lower alkoxy(lower)alkanoyl halide (e.g. methoxyacetyl chloride, ethoxyacetyl chloride), lower alkanoic anhydride (e.g. acetic anhydride, propionic anhydride), benzoic anhydride, etc.

When $R^{1'}$ and $R^{2'}$ each signify an amino group, an N-lower alkylamino group or an N-ar(lower)alkylamino group, the corresponding acylhydrazone compound [I] wherein $R^1$ and $R^2$ are each an acylamino group, an N-lower alkylacylamino group or an N-ar(lower)alkylacylamino group is prepared.

The reaction of the ketone compound [III] with the acylhydrazine compound [IV] is usually carried out in an inert solvent such as an aromatic hydrocarbon (e.g. benzene, toluene, xylene), an amide (e.g. dimethylformamide, dimethylacetamide), an ether (e.g. dioxane, tetrahydrofuran), an alcohol (e.g. ethanol, n-propanol, butanol) or dimethylsulfoxide at a temperature within the range of room temperature to the boiling point of the solvent. In the reaction system, the presence of an acidic substance such as a mineral acid (e.g. hydrochloric acid, sulfuric acid), an organic acid (e.g. acetic acid) or a Lewis acid, or a basic substance such as an alkali metal carbonate, an alkali metal bicarbonate, an alkali metal hydroxide or an organic amine as a catalyst is generally preferred.

As the result of the above reaction, the cylhydrazone compound [I] is produced. Examples of such compound are acetylhydrazone, n-propionylhydrazone, cyclopropylcarbonylhydrazone, cyclohexylcarbonylhydrazone, benzoylhydrazone, chloroacetylhydrazone, bromoacetylhydrazone, phenylacetylhydrazone, phenoxyacetylhydrazone, cinnamoylhydrazone, trifluoroacetylhydrazone, isobutyrylhydrazone and N,N-dimethylcarbamoylhydrazone of the following ketones:

1-[γ-(4-Fluorobenzoyl)propyl]-4-p-chlorophenyl-4-hydroxypiperidine;
1-[γ-(2-Acetamino-4-fluorobenzoyl)propyl]-4-p-chlorophenyl-4-hydroxypiperidine;
1-[γ-(2-Nitro-4-fluorobenzoyl)propyl]-4-p-chlorophenyl-4-hydroxypiperidine;
1-[γ-(4-Fluorobenzoyl)propyl]-4-m-trifluoromethylphenyl-4-hydroxypiperidine;
1[γ-(2,4-Difluorobenzoyl)propyl]-4-m-trifluoromethylphenyl-4-hydroxypiperidine;
1-[γ-(2-Dimethylamino-4-fluorobenzoyl)propyl]-4-m-trifluoromethylphenyl-4-hydroxypiperidine;
1-[γ-(2-Acetamino-4-fluorobenzoyl)propyl]-4-m-trifluoromethylphenyl-4-hydroxypiperidine;
8-[γ-(4-Fluorobenzoyl)propyl]-4-oxo-1-phenyl-1,3,8-triazaspiro[4,5]decane;
8-[γ-(2,4-Difluorobenzoyl)propyl]-4-oxo-1-phenyl-1,3,8-triazaspiro[4,5]decane;
8-[γ-(2-Acetamino-4-fluorobenzoyl)propyl]-4-oxo-1-phenyl-1,3,8-triazaspiro[4,5]decane;
1-[γ-(4-Fluorobenzoyl)propyl]-4-(2-keto-1-benzimidazolinyl)piperidine;
1-[γ-(2,4-Difluorobenzoyl)propyl]-4-(2-keto-1-benzimidazolinyl)piperidine;
1-[γ-(4-Fluorobenzoyl)propyl]-(2-keto-1-benzimidazolinyl)-1,2,3,6-tetrahydropyridine;
1-[γ-(4-Fluorobenzoyl)propyl]-4-o-methoxyphenylpiperazine;
1-[γ-(2,4-Difluorobenzoyl)propyl]-4-o-methoxyphenylpiperazine;

1-[β-(4-Fluorobenzoyl)ethyl]4-o-methoxyphenylpip-
erazine;
1-[γ-(4-Fluorobenzoyl)propyl]-4-phenylpiperazine;
1-[γ-(4-Fluorobenzoyl)propyl]-4-benzyl-4-hydrox-
ypiperidine;
1-[γ-(4-Fluorobenzoyl)propyl]-4-p-tolyl-4-hydrox-
ypiperidine;
1-[β-(4-Fluorobenzoyl)ethyl]-4-p-chlorophenyl-4-
hydroxypiperidine;
1-(γ-Benzoylpropyl)-4-m-trifluoromethylphenyl-4-
hydroxypiperidine;
1-[β-(4-Fluorobenzoyl)ethyl]piperidine;
1-[4-(4-Fluorobenzoyl)butyl]-4-p-chlorophenyl-4-
hydroxypiperidine;
1-[γ-(4-Fluorobenzoyl)propyl]-4-m-trifluoromethyl-
phenyl-4-acetyloxypiperidine;
1-[γ-(2-Propionylamino-4-fluorobenzoyl)propyl]-4-
m-trifluoromethylphenyl-4-hydroxypiperidine;
1-[γ-(2-Benzoylamino-4-fluorobenzoyl)propyl]-4-m-
trifluoromethylphenyl-4-hydroxypiperidine;
1-[γ-(2-Phenoxyacetylamino-4-fluorobenzoyl)-
propyl]-4-p-chlorophenyl-4-hydroxypiperidine;
1-[γ-(2-Phenylacetylamino-4-fluorobenzoyl)propyl]-
4-m-trifluoromethylphenyl-4-hydroxypiperidine;
1-[γ-(4-Fluorobenzoyl)propyl]-4-m-trifluoromethyl-
4-propionyloxypiperidine;
1-(4-Benzoylbutyl)-4-phenylpiperazine;
1-(β-Benzoylethyl)piperidine;
1-(β-Benzoylethyl)-4-phenylpiperazine, etc.

These acylhydrazone compounds [I] in the free base form can be converted into their pharmaceutically acceptable salts such as acid addition salts by treatment with mineral acids (e.g. hydrochloric acid, hydrobromic acid), organic acids (e.g. acetic acid, citric acid, oxalic acid, lactic acid, succinic acid, tartaric acid, cinnamic acid, ascorbic acid) or the like.

Each of the acylhydrazone compounds [I] and their pharmaceutically acceptable salts may be brought into a form suitable for administration according to a method known per se. For the preparation of such form, they may be mixed with carriers or diluents such as water, sesame oil, calcium phosphate, starch, talcum, casein, magnesium stearate, methyl cellulose, polyglycols, tragacanth and the like, sometimes together with stabilizers and/or emulsifying agents. The resulting mixture may be processed in the usual manner to tablets, capsules, pills, ampoules and the like. The usual oral dosage is 0.5 to 200 mg per os daily.

Practical and presently preferred embodiments of the present invention are illustratively shown in the following Examples, which are not intended to limit the scope of the invention thereto.

EXAMPLE 1

To a stirred solution of the 1.5 g of hydrazone of 1-[γ-(4-fluorobenzoyl)propyl]-4-m-trifluoromethylphenyl-4-hydroxypiperidine in 30 ml of dry tetrahydrofuran was added a solution of 0.8 g of propionyl chloride in 10 ml of dry tetrahydrofuran at 0° - 10° C. After stirring was continued for additional 5 hours under cooling below 10° C, the resulting mixture was poured into ice-water, made alkaline with 28% aqueous ammonia and extracted with benzene. The extract was washed successively with dilute aqueous ammonia and saturated aqueous sodium chloride, dried over anhydrous sodium sulfate and evaporated under reduced pressure. The residual solid was recrystallized from ethanol-water to give the propionylhydrazone of 1-[γ-(4-fluorobenzoyl)propyl]-4-m-trifluoromethylphenyl-4-hydroxypiperidine, melting at 128° - 129° C.

EXAMPLE 2

To a stirred solution of the 1.5 g of hydrazone of 1-[γ-(4-fluorobenzoyl)propyl]-4-m-trifluoromethylphenyl-4-hydroxypiperidine in 30 ml of dry tetrahydrofuran was added a solution of 1.5 g of phenoxyacetyl chloride in 10 ml of dry tetrahydrofuran at 0° - 10° C. After stirring was continued for an additional 3 hours under cooling below 10° C, the resulting mixture was poured into ice-water, made alkaline with 28% aqueous ammonia and extracted with benzene. The extract was washed successively with dilute aqueous ammonia and saturated aqueous sodium chloride, dried over anhydrous sodium sulfate and evaporated under reduced pressure. The residual solid was recrystallized from ethanol to give the phenoxyacetylhydrazone of -[γ-(4-fluorobenzoyl)propyl]-4-m-trifluoromethylphenyl-4-hydroxypiperidine, melting at 75° - 78° C.

EXAMPLE 3

In the same manner as in Examples 1 and 2, the following compounds were obtained:
Phenylacetylhydrazone of 1-[γ-(4-fluorobenzoyl)-propyl]-4-m-trifluoromethylphenyl-4-hydroxypiperidine, melting at 150°- 151° C;
Acetylhydrazone of 1-γ-(4-fluorobenzoyl)propyl]-4-m-trifluoromethylphenyl-4-hydroxypiperidine, melting at 163° - 164.5° C;
Benzoylhydrazone of 1-[γ-(4-fluorobenzoyl)propyl]-4-m-trifluoromethylphenyl-4-hydroxypiperidine, melting at 157° - 166° C;
phenoxyacetylhydrazone of 1-[γ-(4-fluorobenzoyl)-propyl]-4-p-chlorophenyl-4-hydroxypiperidine, melting at 151° - 153.5° C;
Propionylhydrazone of 1-[γ-(4-fluorobenzoyl)-propyl]-4-p-chlorophenyl-4-hydroxypiperidine, melting at 143° - 145° C;
Cyclopropylcarbonylhydrazone of 1-[γ-(4-fluorobenzoyl)propyl]-4-p-chlorophenyl-4-hydroxypiperidine, melting at 134° - 144° C;
Cyclopropylcarbonylhydrazone of 1-[γ-(4-fluorobenzoyl)propyl]-4-m-trifluoromethylphenyl-4-hydroxypiperidine, melting at 178.5° - 182° C.

What is claimed is:

1. A compound of the formula:

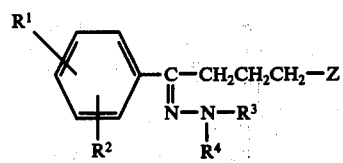

wherein
R$^1$ is halogen, R$^2$ is hydrogen, halogen or benzoylamino of which the benzoyl is optionally substituted with one or two substituents selected from the group consisting of halogen, lower alkyl, lower alkoxy, lower alkanoyl, cyclopropylcarbonyl, cyclohexylcarbonyl, lower alkenoyl, phenyl(lower)alkanoyl, halo(lower)alkanoyl, amino(lower)alkanoyl, phenoxy(lower)-alkanoyl, lower alkylamino(lower)alkanoyl, lower alkoxy(lower)alkanoyl, or phenyl(lower)alkenoyl, R$^3$ is hydrogen or lower alkyl, R$^4$ is benzoyl, lower alkanoyl, phenyl(lower)alkanoyl, cyclopropylcarbonyl, cyclohexylcarbonyl or phenoxy(lower)alkanoyl and Z is a group having the formula:

wherein R⁵ is hydrogen, hydroxyl or benzoyloxy optionally substituted with one or two substituents selected from the group consisting of halogen, lower alkyl, lower alkoxy, lower alkanoyl, cyclopropylcarbonyl, cyclohexylcarbonyl, lower alkenoyl, phenyl(lower)alkanoyl, halo(lower)alkanoyl, amino(lower)alkanoyl, phenoxy(lower)alkanoyl, lower alkylamino(lower)alkanoyl, lower alkoxy(lower)alkanoyl, or phenyl(lower)alkenoyl, and R⁶ is hydrogen, phenyl or benzyl, said phenyl or benzyl being optionally substituted with one or two substituents selected from the group consisting of halogen, lower alkyl, lower alkoxy and trifluoromethyl on the benzene ring;

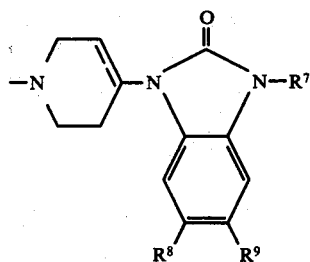

wherein the dotted line indicates the optional presence of an additional single bond linkage, R⁷ is hydrogen or lower alkyl and R⁸ and R⁹ are each hydrogen, halogen or lower alkyl;

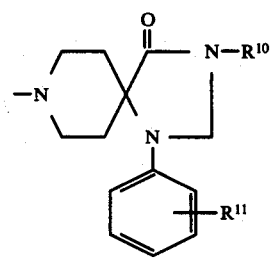

wherein R¹⁰ is hydrogen or lower alkyl and R¹¹ is hydrogen, halogen, lower alkyl or lower alkoxy; or

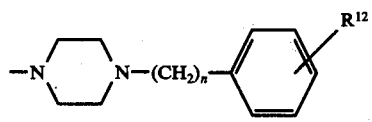

wherein R¹² is hydrogen, halogen, lower alkyl, lower alkoxy or trifluoromethyl and n is an integer of from 0 to 2, or a pharmaceutically acceptable salt thereof.

2. The compound according to claim 1, wherein R¹ is a fluorine atom.

3. The compound according to claim 1, wherein R₂ is a hydrogen atom or a halogen atom.

4. The compound according to claim 1, wherein R¹ is at the para-position.

5. The compound according to claim 1, wherein R¹ is fluorine at the para-position, R² is hydrogen or halogen and R³ is hydrogen.

6. A compound of the formula:

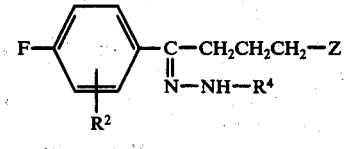

wherein R² is hydrogen or halogen, R⁴ is benzoyl, lower alkanoyl, phenyl(lower)alkanoyl, cyclopropylcarbonyl, cyclohexylcarbonyl or phenoxy(lower)alkanoyl and Z is a group having the formula:

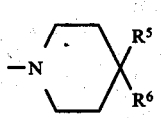

wherein R⁵ is hydrogen, hydroxyl or benzoyloxy optionally substituted with one or two substituents selected from the group consisting of halogen, lower alkyl, lower alkoxy, lower alkanoyl, cyclopropylcarbonyl, cyclohexylcarbonyl, lower alkenoyl, phenyl(lower)alkanoyl, halo(lower)alkanoyl, amino(lower)alkanoyl, phenoxy(lower)alkanoyl, lower alkylamino(lower)alkanoyl, lower alkoxy(lower)alkanoyl, or phenyl(lower)alkenoyl, and R⁶ is hydrogen, phenyl or benzyl, said phenyl or benzyl being optionally substituted with one or two substituents selected from the group consisting of halogen, lower alkyl, lower alkoxy and trifluoromethyl on the benzene ring;

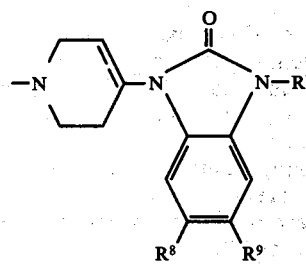

wherein the dotted line indicates the optional presence of an additional single bond linkage, R⁷ is hydrogen or lower alkyl and R⁸ and R⁹ are each hydrogen, halogen or lower alkyl;

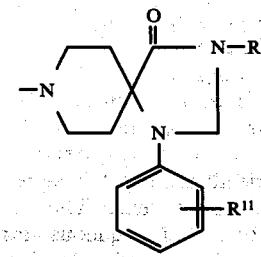

wherein R¹⁰ is hydrogen or lower alkyl and R¹¹ is hydrogen, halogen, lower alkyl or lower alkoxy; or

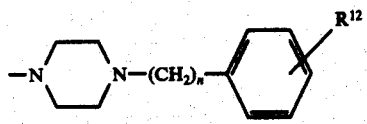 (IV)

wherein R[12] is hydrogen, halogen, lower alkyl, lower alkoxy or trifluoromethyl and n is an integer of from 0 to 2, or a pharmaceutically acceptable salt thereof.

7. A anti-psychotic composition comprising an effective anti-psychotic amount of at least one of the compounds as claimed in claim 1 with at least one pharmaceutically acceptable diluent or carrier.

8. A method for the treatment of psychosis which comprises administering a psychotherapeutically effective amount of the compound as claimed in claim 1 as an active ingredient to a patient.

9. The method according to claim 8, wherein the amount of active compound to be administered is 0.5 to 200 mg. per os daily.

* * * * *